(12) United States Patent
Liebetrau et al.

(10) Patent No.: US 10,836,840 B2
(45) Date of Patent: Nov. 17, 2020

(54) METHOD FOR PRODUCING CROSSLINKED HYALURONIC ACID

(71) Applicant: Merz Pharma GmbH & Co. KGAA, Frankfurt am Main (DE)

(72) Inventors: Wolfgang Liebetrau, Bad Nauheim (DE); Franck Villain, Paris (FR)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 73 days.

(21) Appl. No.: 15/738,609

(22) PCT Filed: Jun. 29, 2016

(86) PCT No.: PCT/EP2016/001110
§ 371 (c)(1),
(2) Date: Dec. 21, 2017

(87) PCT Pub. No.: WO2017/001056
PCT Pub. Date: Jan. 5, 2017

(65) Prior Publication Data
US 2018/0186901 A1    Jul. 5, 2018

(30) Foreign Application Priority Data
Jun. 30, 2015    (EP) .................... 15001939

(51) Int. Cl.
*A61L 27/20* (2006.01)
*C08B 37/08* (2006.01)
*A61L 27/52* (2006.01)
*A61L 27/50* (2006.01)
*A61M 5/00* (2006.01)
*A61M 5/178* (2006.01)

(52) U.S. Cl.
CPC .......... *C08B 37/0072* (2013.01); *A61L 27/20* (2013.01); *A61L 27/50* (2013.01); *A61L 27/52* (2013.01); *A61M 5/002* (2013.01); *A61M 5/178* (2013.01); *A61L 2400/06* (2013.01)

(58) Field of Classification Search
CPC .......... A61L 27/20; A61L 27/50; A61L 27/52; A61L 2400/06; A61M 5/002; A61M 5/178; C08B 37/0072
See application file for complete search history.

(56) References Cited

U.S. PATENT DOCUMENTS

| | | | |
|---|---|---|---|
| 4,582,865 A * | 4/1986 | Balazs ..................... | A61K 8/73 514/781 |
| 7,741,476 B2 | 6/2010 | Lebreton | |
| 9,822,223 B2 | 11/2017 | Barg et al. | |
| 2007/0196426 A1 * | 8/2007 | Hermitte ................. | A61L 27/26 424/426 |
| 2011/0118206 A1 * | 5/2011 | Lebreton .................. | A61K 8/42 514/54 |
| 2015/0262623 A1 | 8/2015 | Barg et al. | |

FOREIGN PATENT DOCUMENTS

WO      2013185934 A1    12/2013
WO      WO-2013185934 A1 *  12/2013

OTHER PUBLICATIONS

Shah et al., Swelling Behavior of Hyaluronic Acid Gels, 1992, Journal of Applied Polymer Science, vol. 45, pp. 293-298. (Year: 1992).*
Zhao et al., Synthesis and Characterization of a novel double crosslinked hyaluronan hydrogel, 2002, Journal of Materials Science: Materials in Medicine, vol. 13, pp. 11-16 (Year: 2002).*
PCT International Search Report for PCT/EP2016/001110, dated Jul. 29, 2016.

* cited by examiner

*Primary Examiner* — Ali Soroush
(74) *Attorney, Agent, or Firm* — McBee Moore & Vanik IP, LLC

(57) ABSTRACT

The present invention relates to the field of hyaluronic acid-based gel compositions suitable for use as soft tissue fillers, and more specifically to a novel method for crosslinking such compositions. The present invention further relates to compositions prepared by the novel crosslinking method and their use in cosmetic and therapeutic applications.

15 Claims, No Drawings

METHOD FOR PRODUCING CROSSLINKED HYALURONIC ACID

CROSS-REFERENCE TO RELATED APPLICATIONS

This application is a National Stage entry of International Application No. PCT/EP2016/001110, filed Jun. 29, 2016, which claims priority to European Patent Application No. 15001939.6, filed Jun. 30, 2015.

BACKGROUND

Field of the Invention

The present invention relates to the field of hyaluronic acid-based gel compositions suitable for use as soft tissue fillers, and more specifically to a novel method for crosslinking such compositions. The present invention further relates to compositions prepared by the novel crosslinking method and their use in cosmetic and therapeutic applications.

Description of Related Art

Hyaluronic acid (HA) is the most important stabilizing component of the extracellular matrix of vertebrate connective tissues, especially skin and mesenchymal tissues. It is a polyanionic glycosaminoglycan (GAG) composed of D-glucuronic add and D-N-acetylglucosamine, linked via alternating $\beta$-1,4 and $\beta$-1,3 glycosidic bonds. HA polymers greatly vary in size and may have a molecular mass ranging from about 5 kDa to about 20,000 kDa in vivo. Under aqueous conditions, HA forms a water-swollen, three-dimensional polymeric network in the form of a gel.

The unique viscoelastic nature and high water-binding capacity of HA together with its biocompatibility and non-immunogenicity has led to its use in a number of clinical applications, including the supplementation of joint fluid in arthritis, as a surgical aid in eye surgery, to facilitate the healing and regeneration of surgical wounds, as a soft tissue filler for cosmetic and therapeutic applications, for drug delivery and in tissue engineering.

Some of these clinical applications require a prolonged in vivo residence time of the HA-based products. However, the in vivo residence time of uncrosslinked ("free") HA is very short. Therefore, HA is often crosslinked to improve durability. During crosslinking, the HA polymer chains are intra- and intermolecularly crosslinked by di-functional or multi-functional crosslinking agents (e.g., aldehydes, epoxides and divinylsulfone) to give a macromolecular crosslinked matrix in the form of a gel. The crosslinking not only results in an improved resistance against in vivo degradation by hyaluronidase or free radicals, but also in enhanced mechanical properties, while maintaining the excellent biocompatibility of the native HA molecules.

Crosslinked hyaluronic acid (HA) is well known for its use as soft tissue dermal filler for aesthetic (cosmetic) and therapeutic applications. For example, dermal fillers are directly injected into the skin for, e.g., filling of wrinkles and augmenting of lips. BDDE (1,4-butanediol diglycidyl ether) is the "golden standard" for use as a crosslinker in the production of soft tissue fillers. Known filler products differ, among others, in their HA concentration, degree of crosslinking, number of crosslinking steps, distribution of crosslinks, monophasic or biphasic nature, average molecular weight and molecular weight distribution of the used HA polymers, and content of additional ingredients, such as antioxidants (e.g., ascorbic acid and derivatives thereof), polyols (e.g., mannitol or glycerol), and local anesthetic agents (e.g., lidocaine).

Various processes for preparing crosslinked gels of HA are known in the art. Generally, these processes for producing crosslinked HA products comprise the steps of mixing a HA starting material and a crosslinking agent under conditions to allow crosslinking to occur, and purifying the crosslinked HA to remove excess crosslinking agent. The specific conditions used for the crosslinking (e.g., the time, temperature, pH, type and amount of crosslinking agent, number of crosslinking steps, as well as molecular weight, type and amount of HA starting materials, etc.) are highly important since they ultimately determine the structure and thus the properties of the crosslinked HA network of the final crosslinked gel.

By way of illustration, European patent No. 1 303 542 discloses a process for the preparation of an injectable hydrogel of at least one crosslinked polymer selected from HA, its salts and their mixtures, characterized in that it comprises the crosslinking of said polymer under the action of at least one polyfunctional crosslinking agent (e.g., BDDE), wherein said polyfunctional crosslinking agent is reacted with said polymer, in the solid state, during hydration; followed by the swelling of said crosslinked polymer by hydration. In an exemplary embodiment, pre-dried fibers of sodium hyaluronate are mixed with a basic BDDE solution and then crosslinked at 50° C. "in the solid state, during hydration".

WO 2010/015900 discloses a method of preparing a soft tissue filler composition, the method comprising the steps of: providing a HA component crosslinked with, e.g., BDDE; adjusting the pH of said HA component to an adjusted pH above about 7.2; and adding a solution containing at least one anesthetic agent (e.g., lidocaine) to said HA component having said adjusted pH to obtain a HA-based soft tissue filler composition. Said crosslinked HA component provided in the first step may be prepared by adding an aqueous BDDE solution to a pre-formed alkaline HA gel (i.e. HA in a pre-swollen state) and subsequent crosslinking at about 50° C. or, alternatively, BDDE can be added directly to the dried HA fibers (i.e. HA polymers in solid state) at the beginning of the process, prior to the hydration, as described in the above-identified European patent No. 1 303 542.

EP 2 236 529 relates to a method for producing crosslinked hyaluronic acid with decreased crosslinking agent. The method comprises crosslinking one or more polymers (i.e. hyaluronic acid, hyaluronate, derivatives thereof and mixtures thereof) with a crosslinking agent at a low temperature of, e.g., between 10° C. to 30° C., under basic conditions for a very long reaction time of greater than 48 hours to obtain a crosslinked hyaluronic acid gel.

U.S. Pat. No. 7,741,476 discloses a process of preparing a crosslinked polymer, comprising the steps of forming a mixture of a first pre-existing HA salt product having a first molecular weight and a second pre-existing HA salt product having a second molecular weight greater than the first molecular weight, and crosslinking the resulting mixture in an aqueous solvent in the presence of an effective and non-excessive amount of at least one crosslinking agent, such that the degree of crosslinking, defined by the ratio: 100×[(total number of reactive groups in said cross-linking agent)/(total number of disaccharide units in the first hyaluronic acid salt and second hyaluronic acid salt)], is theoretically between 0.5 and 70%. The use of a low-molecular weight polymer fraction in association with high-molecular weight polymer fraction is said to afford the possibility of generating, for a non-excessive degree of crosslinking (equivalent to that of the prior art), an injectable monophasic hydrogel having improved mechanical and remanence properties.

However, despite the number of existing crosslinking processes, there is still a need in the art for an improved method of preparing soft tissue filler compositions, and for improved soft tissue filler compositions made by said process which are well-tolerated, offer enhanced longevity, and have excellent mechanical and rheological properties while still being easily injectable through a fine needle.

SUMMARY OF THE INVENTION

According to the present invention, it was unexpectedly found that the above object is solved by a novel crosslinking method combining (a) the use of two HA products with different molecular weights and (b) two crosslinking steps, i.e. a very slight (or "light" or "limited") and a full (or "strong" or "classical") crosslinking step. The thus obtained HA-based soft tissue filler composition exhibits desirable properties for the intended use as soft tissue filler due to its unique three-dimensional network structure.

In a first aspect, the present invention provides a method of preparing a soft tissue filler composition, the method comprising the steps of:
(a) providing a first hyaluronic acid (HA1) product having a first mean molecular weight (MW1) and, separately thereof, a second hyaluronic acid (HA2) product having a second mean molecular weight (MW2), wherein MW1>MW2 or MW1<MW2,
(b) pre-swelling the HA1 product;
(c) crosslinking the pre-swollen HA1 product using 1,4-butanediol diglycidyl ether (BDDE) as crosslinking agent under conditions to allow limited crosslinking so as to obtain a lightly crosslinked HA1 gel composition;
(d) pre-swelling the HA2 product;
(e) mixing the lightly crosslinked HA1 gel composition with the pre-swollen HA2 product; and
(f) crosslinking the mixture of the lightly crosslinked HA1 gel composition and the pre-swollen HA2 product using BDDE as crosslinking agent so as to obtain a crosslinked HA1/HA2 gel composition.

In another aspect, the present invention provides a soft tissue filler composition obtainable by the method according to the present invention.

In a further aspect, the present invention provides a kit, comprising a syringe and, separately thereof, the soft tissue filler composition of the present invention, or a syringe prefilled with the soft tissue filler composition of the present invention.

In a still further aspect, the present invention relates to the use of the soft tissue filler composition for cosmetic applications, such as the treatment of facial wrinkles.

In yet another aspect, the present invention provides a soft tissue filler composition as described herein for use in therapy, in particular for use in treating stress urinary incontinence, vesico-ureteral reflux, vocal fold insufficiency, and vocal fold medialization.

Preferred embodiments of the present invention are set forth in the appended claims.

DETAILED DESCRIPTION OF A PREFERRED EMBODIMENT

The inventors of the present invention have unexpectedly found that the use of two HA products with different molecular weights that are crosslinked in a specific manner involving a very limited (or "slight" or "light") crosslinking step and a "classical" (or "full") crosslinking step improves the crosslinking and results in a crosslinked product which not only exhibits a long in vivo residence time but also has favorable properties for use as a soft tissue filler.

In particular, it was surprisingly found that crosslinking of (i) lightly crosslinked HA, prepared by slight (i.e. very limited) crosslinking of a first HA product (HA1) having a first molecular weight, and (ii) a second uncrosslinked HA product (HA2) having a second molecular weight higher than the first molecular weight enables the preparation of a soft tissue filler composition having a unique network structure of crosslinked HA polymer molecules. Advantageously, the use of two different HA products, and in varying ratios, as well as the specific crosslinking technique of the present invention enables the characteristics of the soft tissue filler composition to be tailored to its intended purpose.

Due to its unique structure, the soft tissue filler prepared in accordance with the method of the present invention provides a number of advantages over known fillers, including excellent biocompatibility, no immunogenicity, high moisture retention, improved in vivo remanence, low extrusion force (ease of injectability), as well as desirable mechanical and rheological properties for use as a soft tissue filler, such as a high volumizing capacity.

Without being bound by theory, it is believed that the light crosslinking step primes HA1 for the later "classical" or "full" crosslinking of a mixture of slightly crosslinked HA1 and uncrosslinked HA2. In particular, the light crosslinking step is believed to result in mechanical relaxation of the coiled HA polymer chains. The relaxed or "stretched" HA molecules are thought to be more easily accessible by BDDE molecules, thereby ensuring better homogeneity and efficacy of a subsequent crosslinking. It may be hypothesized that the very limited generation of crosslinks leads to a restricted segmental motion of HA polymer chains, thereby influencing the performance of chemical crosslinking using BDDE. In particular, it is believed that the improved efficacy of crosslinking is due to the better accessibility of the HA polymers for BDDE, thereby desirably enabling the use of less crosslinker (i.e. BDDE) while still achieving the same crosslinking degree.

In a first aspect, the present invention provides a method of preparing a soft tissue filler composition. The method comprises steps (a) to (f) and involves slightly crosslinking a first pre-swollen HA (HA1) product, mixing the slightly crosslinked HA1 product with a second pre-swollen HA (HA2) product, and crosslinking the resulting mixture using BDDE as crosslinking agent.

The term "soft tissue filler composition", as used herein, is intended to mean a composition that is used or suitable for use as a soft tissue filler. A "soft tissue filler" within the meaning of the present invention refers to a material designed to add volume to areas of soft tissue deficiency. The term "soft tissue" generally relates to tissues that connect, support, or surround other structures and organs of the body. In the present invention, soft tissue includes, for example, muscles, tendons (bands of fiber that connect muscles to bones), fibrous tissues, fat, blood vessels, nerves, and synovial tissues (tissues around joints). Applications of soft tissue fillers include, but are not limited to dermocosmetic applications, such as adding fullness to the lips, augmenting cheeks, treating skin lines or wrinkles, or therapeutic applications, such as increasing the volume of other tissues in need thereof such as the sphincter, the urethra or the vocal cords.

In the context of the present invention, the soft tissue filler is preferably a dermal filler composition. A "dermal filler composition" within the meaning of the present invention is generally a substance that adds volume to cells under the skin leading to, e.g., smoothened skin wrinkles, augmented lips, improved skin appearance, or treated scars. It is generally used in the dermis area, such as below the epidermis or above the hypodermis and as such may be injected subcutaneously, hypodermically or intradermally, or some combinations.

According to the present invention, the soft tissue filler composition is a gel. The term "gel", as used herein, generally refers to a material having fluidity at room or body temperature between that of a liquid and solid. In addition, the term "gel" is intended to mean a material capable of absorbing water (i.e. a "hydrogel"). Within the present invention, the soft tissue filler composition generally comprises a physiologically acceptable carrier fluid, particularly an apyrogenic isotonic buffer, more particularly a physiological saline solution or a buffered physiological saline solution.

The soft tissue filler composition of the present invention is further "injectable". This means that the soft tissue filler composition is suitable for injection into the skin or other tissue in order to bring the soft tissue filler composition to the desired target site. An "injectable" composition within the meaning of the present invention can be dispensed from syringes under normal conditions under normal pressure.

In step (a) of the method according to the present invention, there is provided a first hyaluronic acid (HA1) product having a first mean molecular weight (MW1) and, separately thereof, a second hyaluronic acid (HA2) product having a second mean molecular weight (MW2), wherein MW1>MW2 or MW1<MW2. The HA1 product may be provided prior to, concurrent with, or after the provision of the HA2 product. Preferably, MW1 is <MW2. Furthermore, |MW1-MW2| (i.e. the absolute, non-negative value of the difference of MW1 and MW2) is preferably $\geq 0.5 \times 10^6$ Da, more preferably from $0.8 \times 10^6$ Da to $3.5 \times 10^6$ Da, particularly preferred from $1.0 \times 10^6$ Da to $2.5 \times 10^6$ Da, and most preferably from $1.2 \times 10^6$ Da to $2.0 \times 10^6$ Da.

In particular, if MW1 is <MW2, HA1 has preferably a first mean molecular weight (MW1) of between $1.0 \times 10^6$ Da and $2.0 \times 10^6$ Da, more preferably between $1.2 \times 10^6$ Da and $4.0 \times 10^6$ Da and most preferably between $1.2 \times 10^6$ Da and $4.0 \times 10^6$ Da, and HA2 has preferably a second mean molecular weight (MW2) of between $2.5 \times 10^6$ Da and $4.5 \times 10^6$ Da, preferably between $2.5 \times 10^6$ Da and $4.5 \times 10^6$ Da and most preferably between $2.5 \times 10^6$ Da and $4.5 \times 10^6$ Da. Particularly suitable for use within the present invention is a combination of a HA1 having a first mean molecular weight (MW1) of between $1.0 \times 10^6$ Da, and $2.0 \times 10^6$ Da and a HA2 having a second mean molecular weight (MW2) of between $2.5 \times 10^6$ Da and $3.5 \times 10^6$ Da.

Alternatively, if MW1 is >MW2, HA1 has preferably a first mean molecular weight (MW1) of between $2.5 \times 10^6$ Da and $4.5 \times 10^6$ Da, preferably between $2.5 \times 10^6$ Da and $4.5 \times 10^6$ Da and most preferably between $2.5 \times 10^6$ Da and $4.5 \times 10^6$ Da, and HA2 has preferably a second mean molecular weight (MW2) of between $1.0 \times 10^6$ Da and $2.0 \times 10^6$ Da, more preferably between $1.2 \times 10^6$ Da and $4.0 \times 10^6$ Da and most preferably between $1.2 \times 10^6$ Da and $4.0 \times 10^6$ Da. Particularly suitable for use within the present invention is a combination of a HA1 having a first mean molecular weight (MW1) of between $2.5 \times 10^6$ Da and $3.5 \times 10^6$ Da, and a HA2 having a second mean molecular weight (MW2) of between $1.0 \times 10^6$ Da and $2.0 \times 10^6$ Da.

All numbers herein expressing "molecular weight", "molecular mass", "mean molecular weight" or "mean molecular mass" of HA are to be understood as indicating the number-average molar mass $M_n$ (also referred to as number-average molecular weight (NAMW)) in Daltons (Da). The number average molecular mass is the ordinary arithmetic mean or average of the molecular masses of the individual HA polymer molecules. It is defined as the molecular mass of n polymer molecules, summing the masses $M_i$ for each polymer species Ni according to the following formula: $M_n = \Sigma_i N_i M_i / \Sigma_i N_i$.

Various methods can be applied herein to determine the molecular weight of HA, such as intrinsic viscosity measurements (e.g., European Pharmacopoeia 7.0—Hyaluronic Acid monograph No. 1472, January 2011), capillary electrophoresis (CE) (e.g., according to Kinoshita et al., Biomed. Chromatogr., 2002, 16:141-45), gel permeation chromatography (GPC) (e.g., according to Kim et al., Food Chem., 2008, 109:63-770), and multi-angle laser light scattering combined with size-exclusion chromatography (SEC-MALLS) (e.g., in accordance to Hokputsa et al., Eur. Biophys. J. Biophys. Lett., 2003, 32:450-456).

Within the framework of the present invention, the number average molecular mass ($M_n$) of HA polymers is preferably determined by gel permeation chromatography (GPC) or viscometry via the Mark-Houwink equation. The GPC technique involves forcing a polymer solution through a matrix of crosslinked polymer particles at a pressure of up to several hundred bar. As well known to a skilled person, the use of low dispersity standards allows one to correlate retention time with molecular mass.

The Mark-Houwink equation gives a relation between intrinsic viscosity (η) and molecular weight M and allows determination of the molecular weight of a polymer from data on the intrinsic viscosity and vice versa. Within the context of the present invention, the intrinsic viscosity is preferably measured according to the procedure defined in European Pharmacopoeia 7.0 (Hyaluronic Acid monograph No. 1472, January 2011). For calculation of the molecular weight of HA from intrinsic viscosity data, the following Mark-Houwink is used within the framework of the present invention:

$$[\eta] = K \times M^a,$$

wherein [η]=intrinsic viscosity in m³/kg, M=molecular weight, K=$2.26 \times 10^{-5}$, and a=0.796.

In accordance with the present invention, the intrinsic viscosity of HA1, if MW1 is <MW2, is preferably between 1350 ml/g and 2350 ml/g and the intrinsic viscosity of HA2 is preferably between 2800 ml/g and 4500 ml/g. If MW1 is >MW2, the intrinsic viscosity of HA1 is preferably between 2800 ml/g and 4500 ml/g and the intrinsic viscosity of HA2 is preferably between 1350 ml/g and 2350 ml/g.

The molecular weight distribution of HA1 and HA2 may be defined by its polydispersity index (PDI). The PDI of a polymer sample is defined as PDI=$M_w/M_n$, where $M_w$ is the mass-average molar mass (or molecular weight; $M_w = \Sigma_i N_i M_i^2 / \Sigma_i N_i M_i$) and $M_n$ is the number-average molar mass (or molecular weight; $M_n = \Sigma_i N_i M_i / \Sigma_i N_i$). In the context of the present invention, the PDI of HA1 and HA2, independently of each other, generally falls within the range of >1.0 (e.g., 1.05 or 1.1) to 1.6 (e.g., 1.5 or 1.45). Preferably, the polydispersity index of both HA1 and HA2 is in the range of 1.1 to 1.45, in particular in the range of 1.2 to 1.4.

Within the present invention, there is preferably no overlap between the molecular weight distribution of the HA1 and HA2 products or only a small overlap corresponding to less than 20 wt. %, preferably less than 10 wt. % or less than 5 wt. % of the total weight of HA1 and HA2 used in the method according to the present invention. In other words, no or only a small fraction of the HA polymers of HA1 and HA2 have the same molecular weight, while the majority of the HA polymers of HA1 and HA2 center around the average molecular weight of HA1 and HA2, respectively, and thus differ in their molecular weights.

The weight ratio of HA1 to HA2 is generally from 1:99 to 99:1, for example from 10:90 to 90:10 or from 50:50 to 99:1, preferably from 60:40 to 95:5, more preferably from 70:30 to 95:5, and most preferably from 80:20 to 90:10. Adjusting the weight ratio of HA1 to HA2 allows for the fine-tuning of desirable properties for the intended purpose of the soft tissue filler composition.

In step (b) of the method according to the present invention, the HA1 product is subjected to pre-swelling. The swelling is usually carried out in neutral pH (i.e. around pH 7.0, e.g., 6.0 to 8.0) for about 10 h to 20 h, e.g., 12 h. The HA1 is typically dissolved in water at, e.g., room temperature (20° C. to 25° C.) for some hours (e.g. 5 to 20 h). Preferably, the pre-swelling step is carried out under conditions such that the pre-swelling ratio (PSR), defined as the weight of the pre-swollen HA1 obtained in step (b) to the weight of HA1 prior to pre-swelling step (b) is between 20 and 200.

The term "pre-swelling ratio", as used herein, preferably refers to the ratio of the weight of the HA1 and HA2 products after pre-swelling in steps (b) and (d), respectively, to the weight of the pre-swollen HA1 and HA2 without any bound water, i.e. the dry weight. The swelling ratio may be determined by taking a sample of the pre-swollen HA product, removing excess water on the surface, measuring the weight of the gel ($W_{wet}$), drying the sample by heating (e.g., at 120° C. for 1 h) to remove bound water, and measuring the weight of the dried HA sample ($W_{dry}$). The pre-swelling ratio is then calculated as follows:

$$PSR = [W_{wet}/W_{dry}] \times 100\%.$$

In step (c) of the method according to the present invention, the pre-swollen HA1 product is crosslinked using 1,4-butanediol diglycidyl ether (BDDE) as crosslinking agent under conditions to allow limited crosslinking so as to obtain a lightly crosslinked HA1 gel composition.

The BDDE crosslinking agent is preferably applied in an aqueous alkaline solution, for example, in the form of a BDDE containing NaOH solution, as known in the art. The slight crosslinking is achieved by appropriately choosing crosslinking-limiting conditions, as known to those skilled in the art.

In accordance with the present invention, the limited crosslinking step (c) is preferably carried out under conditions satisfying one or more (e.g. one, two, three, four, five, six or seven) of the following:

$\%m_{BDDE}$=<15%, preferably <10%, more preferably <5%, and most preferably <3% (i)

wherein:
% $m_{BDDE}$ is the percent weight ratio of the total weight of BDDE used in crosslinking step (c) to the total weight of BDDE used in crosslinking steps (c) and (f), $R=(m_{BDDE}/m_{HA1})\times 100\%$=0.1% to 4.0%, preferably 0.5% to 3.0%, more preferably 1.5% to 2.5%, and most preferably 2.0% (ii)

wherein:
R is the crosslinker ratio,
$m_{BDDE}$ is the total weight of BDDE used in crosslinking in step (c), and
$m_{HA1}$ is the total weight of HA1 subjected to crosslinking step (c), $X=(N_{BDDE}\times 2)/N_{DU}\times 100\%$=0.5% to 15%, preferably 2.0% to 12%, more preferably 6% to 10%, and most preferably 8% (iii)

wherein:
X is the calculated theoretical maximal degree of crosslinking,
$N_{BDDE}$ is the total number of BDDE molecules used in crosslinking step (c), and
$N_{DU}$ is the total number of disaccharide units (DU) of the HA1 subjected to crosslinking step (c),

[HA1]=<100 mg/ml, preferably <50 mg/ml, more preferably <25 mg/ml, and most preferably <10 mg/ml (iv)

wherein:
[HA1] is the first hyaluronic acid (HA1) concentration prior to crosslinking, T=≤30° C., preferably 20° C., more preferably 10° C. and 30° C. or 15° C. and 25° C., and most preferably between 20° C. to 25° C., (v)

wherein:
T is the crosslinking temperature, t=0.25 h to 4.0 h, preferably 0.5 h to 2.0 h, more preferably 0.5 h to 1.5 h, and most preferably 0.5 h to 1.0 h (vi)

wherein:
t is the crosslinking time, and pH≤10, preferably 7.0 to 10.0, more preferably 8.0 to 10.0, and most preferably 9.0 to 10.0. (vii)

The crosslinking step (c) may, for example, be carried out using the following conditions: T=20° C. to 30° C. and t=0.25 h to 1.0 h, or T=10° C. to <20° C. and t=0.5 to 3.0 h. Furthermore, the crosslinking may be controlled by the HA concentration since the higher the HA content the better the crosslinking. Thus, in crosslinking step (c), a quite diluted HA solution may be advantageously used, as defined in condition (i). The crosslinking in step (c) may be terminated by, e.g., cooling down the crosslinking reaction mixture to a temperature of about 5° C.

In step (d) of the method according to the present invention, the HA2 product is subjected to pre-swelling. The timing of the pre-swelling is not particularly limited and may be carried out either prior, during and/or after crosslinking step (c). Typically, the swelling is carried out in neutral pH (i.e. around pH 7.0, e.g., 6.0 to 8.0) for about 10 h to 20 h, e.g., 12 h, and then an alkaline BDDE solution is added. Preferably, the HA2 is dissolved in water at, e.g., room temperature (20° C. to 25° C.) for some hours (e.g. 5 to 20 h). Furthermore, the HA2 product is preferably pre-swollen in step (d) such that the pre-swelling ratio (PSR), defined as the weight of the pre-swollen HA2 obtained in step (d) to the weight of HA2 prior to pre-swelling step (d), is between 20 and 200.

In step (e) of the method according to the present invention, the lightly crosslinked HA1 gel composition is mixed with the pre-swollen HA2 product.

In step (f) of the method according to the present invention, the mixture of the lightly crosslinked HA1 gel composition and the pre-swollen HA2 product is crosslinked using BDDE as crosslinking agent so as to obtain a crosslinked HA1/HA2 gel composition. This crosslinking step corresponds to "classical" crosslinking of HA gels using BBDE as crosslinking agent as conventionally carried out in the art. The crosslinking conditions are adjusted to obtain a degree of crosslinking such that the final product is suitable for use as a soft tissue filler, especially as a dermal filler, as known in the art.

For example, the crosslinking reaction may be conducted at temperatures between 30° C. and 60° C. and for reaction times between 1.0 h and 20 h, preferably between 2 h and 10 h. The yields of crosslinked HA increase with the increase in reaction temperature up to about T=60° C. At higher temperatures, however, the reaction yield declines due to the prevalence of hydrolysis processes associated with the basic reaction medium. Furthermore, increasing the reaction times causes an increase in the yield, which is particularly marked in the first hours, when about 70% of the crosslinked HA is formed. Therefore, reaction times of 1 h to 10 h, in particular 2 h to 6 h or 3 h to 5 h are preferred since they represent a good compromise between the reaction yield and the process time.

The BDDE used in the crosslinking step (f) is generally the sum of unreacted BDDE of the first crosslinking step (i.e. step (c)) and "fresh" BDDE added in the second crosslinking step (i.e. step (f)). However, it is also contemplated that no additional BDDE is added in the second crosslinking step (i.e. step (f)), and the remaining amount of unreacted BDDE of the first crosslinking step is sufficient, under appropriate reaction conditions, to result in the desired crosslinking degree. For example, a relatively high amount of BDDE but suboptimal reaction conditions may be used in crosslinking step (c) which leaves behind a high amount of unreacted BDDE. This amount of unreacted BDDE may then, under better or optimal reaction conditions, result in the desired strong crosslinking of step (f).

In accordance with the present invention, the "classical" crosslinking step (f) resulting in the highly crosslinked HA1/HA2 gel composition is preferably carried out under conditions satisfying one or more (i.e. one, two, three or four) of the following (if BDDE is added in step (f), the "used" BDDE refers to the BDDE "added" in step (f)):

$$R=(m_{BDDE}/m_{HA2})\times 100\% = 2\% \text{ to } 12\%, \text{ preferably } 4\% \text{ to } 10\%, \text{ more preferably } 6\% \text{ to } 10\%, \text{ and most preferably } 8\% \qquad (i')$$

wherein:
R is the crosslinker ratio,
$m_{BDDE}$ is the total weight of BDDE used in crosslinking step (f), and
$m_{HA2}$ is the total weight of HA2 subjected to crosslinking step (f), $$X=[(N_{BDDE}\times 2)/N_{DU}]\times 100\% = 10\% \text{ to } 50\%, \text{ preferably } 15\% \text{ to } 40\%, \text{ more preferably } 20\% \text{ to } 35\%, \text{ and most preferably } 30\% \qquad (ii')$$

wherein:
X is the calculated maximal degree of crosslinking,
$N_{BDDE}$ is the total number of BDDE molecules used in crosslinking step (f),
$N_{DU}$ is the total number of disaccharide units (DU) of HA2 subjected to crosslinking step (f), $$MoD=[(N_{MONO}+N_{DOUBLE})/N_{DU}]\times 100\% = 1.0\% \text{ to } 25\%, \qquad (iii')$$

wherein:
M is the degree of modification,
$N_{MONO}$ is the total number of mono-linked BBDE molecules,
$N_{DOUBLE}$ is the total number of double-linked BBDE molecules, and
$N_{DU}$ is the total number of disaccharide units (DU) of HA1 subjected to crosslinking step (c) and HA2 subjected to crosslinking step (f), and $$\% M_{BDDE} = \geq 85\%, \text{ preferably } \geq 90\%, \text{ more preferably } \geq 95\%, \text{ and most preferably } \geq 97\% \qquad (iv')$$

wherein:
% $M_{BDDE}$ is the percent ratio of the total weight of BDDE used in crosslinking step (f) to the total weight of BDDE used in crosslinking steps (c) and (f).

The BDDE-crosslinked hyaluronic acid may have a degree of modification (MoD), expressed as the ratio of the sum of mono- and double-linked BDDE-crosslinkers to the sum of hyaluronic acid disaccharide units, of 1.0% to 25%, preferably 1.0% to 20%, more preferably 2.0% to 15%, particularly preferable 3.0% to 10%, and most preferably 3.0% to 8.0% or 4.0% to 7.0%.

The degree of modification can be determined by NMR in accordance with methods known in the art (Edsman et al., Gel Properties of Hyaluronic Acid Dermal Fillers, Dermatol. Surg. 2012, 38:1170-1179; Guarise et al., SEC determination of cross-link efficiency in hyaluronan fillers, Carbohydrate Polymers 2012, 88:428-434; Kenne et al., Modification and cross-linking parameters in hyaluronic acid hydrogels—Definitions and analytical methods, Carbohydrate Polymers 2013, 91:410-418).

In brief, the dialyzed and sterilized gels are degraded before conducting the NMR measurement. The degradation can be performed by chondroitinase AC (Edsman et al., supra; Kenne et al., supra), NaOH (Guarise et al., supra), addition of hyaluronidase (e.g., 150 U ovine hyaluronidase to 1 g of gel) or by incubation at 90° C. for at least 35 h. The obtained solutions are then lyophilized, dissolved in $D_2O$, and well homogenized.

The NMR measurement can be performed at, e.g., 500 MHz, at a pulse of 20 degree with several repetitions at ambient temperature to receive a spectrum with appropriate resolution. In accordance with the literature, the degree of modification (MoD) is assessed by calculating the ratio of the N-acetyl signals of HA to the methylene signals of BDDE. For N-acetyl of HA, the critical signals are located at about 2.0 ppm and at about 1.6 ppm for BDDE when solubilized in $D_2O$. In order to calculate the degree of modification, the integral values were identified and the ratio of protons of 3H of N-acetyl ($CH_3$) to 4H of methylene ($CH_2CH_2$) needs to be taken in account, in accordance with the literature (Edsman et al., supra, and Kenne et al., supra).

In accordance with the present invention, the crosslinked HA1/HA2 gel composition obtained in step (f) may be subjected to neutralization by, e.g., using an acid (e.g., HCl) to terminate the crosslinking reaction of step (f). In addition, or alternatively, the crosslinking may be terminated by cooling the reaction mixture to a temperature of, e.g., 5° C. and/or removing the unreacted BDDE crosslinker by dialysis. In order to purify the gel, the method may further comprise a step of subjecting the crosslinked HA1/HA2 gel composition obtained in step (f) to dialysis.

In addition, the method of the present invention may further comprise a step of sterilizing the crosslinked HA1/HA2 gel composition, optionally after having been filled into a syringe, by moist heat.

Furthermore, the method of the present invention may further comprise one or both of the following steps:
adding one or more compounds, selected from the group consisting of local anesthetic agents, polyalcohols, vitamins, alkali metal and alkaline earth metal salts, metals, antioxidants, amino acids, and ceramic particles, to the crosslinked HA1/HA2 gel composition, and adjusting the pH to about 6.4 to 7.8.

Within the context of the present invention, the addition of a local anesthetic is particularly desirable in view of its ability to mitigate pain upon injection. Exemplary local anesthetic agents include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, betaeucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof.

Preferably, the anesthetic agent is lidocaine, such as in the form of lidocaine HCl. The compositions prepared by the method of the present invention may have a lidocaine concentration of, for example, 0.05 wt. % to 5.0 wt. %, 0.1 wt. % to 4.0 wt. %, 0.2 wt. % to 3.0 wt. %, 0.3 wt. % to 2.0 wt. %, or 0.4 wt. % to 1.0 wt. %.

Suitable polyols for use herein include, but are not limited to, glycerol, mannitol, sorbitol, propylene glycol, erythritol, xylitol, maltitol, and lactitol. Particularly suitable for use herein is mannitol and glycerol. Further, the polyol is preferably glycol, optionally in combination with one or more of the aforementioned polyol compounds, in particular mannitol. The polyol(s) may, for example, be included in the injectable dermal filler composition in a concentration of 0.1% to 25% or 1% to 20% or 2% to 15% volume/volume, particularly in a concentration of 5% to 10% volume/volume.

Suitable vitamins include vitamin C, vitamin E and vitamins of the B group, i.e. one or more of $B_1$, $B_2$, $B_3$, $B_5$, $B_6$, $B_7$, $B_9$ and $B_{12}$ vitamins. The concentration of vitamin C or of vitamin E is preferably from about 0.01 mg/ml to about 10.0 mg/ml, more preferably from about 0.1 mg/ml to about 5.0 mg/ml, and the total concentration of the vitamins of the B group is preferably from about 0.01 mg/ml to about 10.0 mg/ml, more preferably from about 0.1 mg/ml to about 5.0 mg/ml. The vitamins may be present to stimulate and maintain cellular metabolism and, thus, to promote collagen production. Particularly preferred for use here is vitamin C, vitamin E and vitamin $B_6$.

A preferred salt for use in the soft tissue filler composition is a zinc salt. The ceramic particles are preferably hydroxyapatite particles, e.g., calcium hydroxyl apatite (CaHA) particles.

It is further contemplated herein that the injectable dermal filler composition may include non-crosslinked HA. In particular, the soft tissue filler composition may further comprise 0.001% to 15%, in particular 1% to 10% volume/volume non-crosslinked hyaluronic acid. The molecular weight of said non-crosslinked hyaluronic acid is preferably between $3.0 \times 10^5$ Da and $4.0 \times 10^6$ Da, in particular between $1.0 \times 10^6$ Da and $3.0 \times 10^6$ Da. Preferably, the soft tissue filler composition of the present invention lacks any crosslinked polymers other than the crosslinked HA described herein and, more preferably, also lacks any non-crosslinked polymers other than non-crosslinked (i.e. free) HA.

In another aspect, the present invention relates to a soft tissue filler composition obtainable by the method according to the present invention. The concentration of HA in the soft tissue filler composition may range from 1 mg/ml to 50 mg/ml. Typically, the concentration of HA is between 5 mg/ml and 40 mg/ml or between 10 mg/ml and 35 mg/ml, particularly between 15 mg/ml to 30 mg/ml or between 20 mg/ml to 25 mg/ml.

In yet another aspect, the present invention relates to a kit, comprising a syringe and, separately thereof, the soft tissue filler composition of the present invention. The present invention also relates to a kit, comprising a syringe prefilled with the soft tissue filler composition of the present invention. The kit may also comprise instructions for use.

In a further aspect, the present invention relates to the use of a soft tissue filler composition according to the present invention in cosmetic applications, e.g., for improving the visual appearance, in particular of the face. Cosmetic applications include, but are not limited to, augmenting or filling of wrinkles and lines of the skin, in particular of facial lines and facial wrinkles, e.g., of glabellar lines, nasolabial folds, chin folds, marionette lines, buccal commissures, peri-oral wrinkles, and crow's feet. Other exemplary cosmetic applications include filling cutaneous depressions, masking scars and temples, providing subdermal support of the brows, malar and buccal fat pads, treating tear troughs, nose, chin and jawline corrections, increasing the volume of the lips, augmenting cheeks, treating the perioral region, infraorbital region and facial asymmetries, and/or improve skin hydration and skin texture.

In a still further aspect, the present invention relates to a soft tissue filler composition of the present invention in for use in therapy. In particular, the soft tissue filler composition of the present invention may be used in treating stress urinary incontinence, vesico-ureteral reflux, vocal fold insufficiency, and vocal fold medialization.

The soft tissue filler composition of the present invention is generally administered in an effective amount to a subject by injection, such as by subcutaneous or intradermal injection. For example, the composition may be intradermally or subcutaneously injected using the serial puncture technique. The term "effective amount" refers to the amount of the (injectable) soft tissue filler composition sufficient to effect beneficial or desired cosmetic (aesthetic) or therapeutic results. A "subject" in the sense of the present invention is any individual or patient, usually a human, in need of the treatment of a particular condition or disease.

The present invention will now be further illustrated by the following, non-limiting example.

EXAMPLES

In the example provided below, a soft tissue filler composition is prepared in accordance with the method of the present invention.

Example 1

Preparation of a Composition of the Present Invention Using a Temperature-Limited Crosslinking Step A first sodium hyaluronate (NaHA1) having a molecular weight of 1.5 MDa was dissolved in water, followed by stirring for 12 hours at room temperature. In parallel, a second sodium hyaluronate (NaHA2) having a molecular weight of 2.8 MDa was dissolved in water and also stirred for 12 hours at room temperature.

Next, an aqueous alkaline NaOH/BDDE solution (AS1) was prepared by dissolving a given amount of BDDE in an aqueous alkaline NaOH solution. A portion of AS1 was added to the hydrated (pre-swollen) NaHA1, and the mixture was stirred in a mixing bowl at 5° C. and 500 rpm for 10 to 15 minutes. The mixing speed was then lowered to 100 rpm and the temperature set point was changed to a temperature of 20° C. After a temperature of 18° C. had been reached, the mixing was turned off, and the contents were allowed to react for 0.5 hours. The (limited) crosslinking reaction was then quenched by lowering the temperature to 5° C.

Another aqueous alkaline NaOH/BDDE solution (AS2) was prepared by dissolving a given amount of BDDE in an aqueous alkaline NaOH solution. A portion of AS2 and the hydrated (pre-swollen) NaHA2 were added to the contents of the mixing bowl and the resulting mixture was stirred at 5° C. and 500 rpm for about 2 hours. The mixing speed was then lowered to 100 rpm and the temperature set point was changed to a temperature of 50° C. After a temperature of 47° C. had been reached, the mixing was turned off, and the contents were allowed to react for 3 hours. In this second crosslinking step, the amount of BDDE added was about fifteen times the amount used in the first limited crosslinking step.

The crosslinking reaction was terminated by addition of a 1M HCl solution (quench solution) and subsequent cooling to 5° C. A final stirring step for about 10 to 15 minutes at 500 rpm yielded a crosslinked gel composition that may then be further processed as desired. For example, the gel may advantageously be cut into pieces, extruded through screens, dialyzed, degassed, extruded into syringes and steam sterilized by autoclaving. The thus obtained sterile HA gel product is, among others, suitable for use as dermal filler, such as in correction of skin wrinkles or augmentation of cheeks or lips.

The invention claimed is:

1. A method of preparing a soft tissue filler composition, the method comprising:
   (a) providing a first hyaluronic acid (HA1) product having a first mean molecular weight (MW1) and, separately thereof, a second hyaluronic acid (HA2) product having a second mean molecular weight (MW2), wherein MW1>MW2 or MW1<MW2;
   (b) pre-swelling the HA1 product;
   (c) crosslinking the pre-swollen HA1 product using 1,4-butanediol diglycidyl ether (BDDE) as crosslinking agent under conditions to allow limited crosslinking so as to obtain a lightly crosslinked HA1 gel composition;
   (d) pre-swelling the HA2 product;
   (e) mixing the lightly crosslinked HA1 gel composition with the pre-swollen HA2 product; and
   (f) crosslinking the mixture of the lightly crosslinked HA1 gel composition and the pre-swollen HA2 product using BDDE as crosslinking agent so as to obtain a crosslinked HA1/HA2 gel composition, wherein $$\%M_{BDDE} = \geq 85\%$$

wherein:
% $M_{BDDE}$ is the percent ratio of the total weight of BDDE used in crosslinking (f) ($M_{BDDE}$) to the total weight of BDDE used in crosslinking (c) and (f).

2. The method of claim 1, wherein $|MW1-MW2| \geq 0.5 \times 10^6$ Da.

3. The method of claim 1, wherein HA1 has a first mean molecular weight (MW1) of between $1.0 \times 10^6$ Da and $2.0 \times 10^6$ Da and HA2 has a second mean molecular weight (MW2) of between $2.5 \times 10^6$ Da and $4.5 \times 10^6$ Da, or wherein HA1 has a first mean molecular weight (MW1) of between $2.5 \times 10^6$ Da and $4.5 \times 10^6$ Da and HA2 has a second mean molecular weight (MW2) of between $1.0 \times 10^6$ Da and $2.0 \times 10^6$ Da.

4. The method of claim 1, wherein the intrinsic viscosity of HA1 is between 1350 ml/g and 2350 ml/g and the intrinsic viscosity of HA2 is between 2800 ml/g and 4500 ml/g, or wherein the intrinsic viscosity of HA1 is between 2800 ml/g and 4500 ml/g and the intrinsic viscosity of HA2 is between 1350 ml/g and 2350 ml/g.

5. The method of claim 1, wherein HA1 and HA2 have a molecular weight distribution characterized by a polydispersity index (PDI) of $1.0 < PDI \leq 1.6$.

6. The method of claim 1, wherein the weight ratio of HA1 to HA2 is from 60:40 to 95:5.

7. The method of claim 1, wherein the HA1 product is pre-swollen in (b) such that a pre-swelling ratio (PSR), defined as the weight of the pre-swollen HA1 obtained in (b) to the weight of HA1 prior to pre-swelling (b) is between 20 and 200, and/or wherein the HA2 product is pre-swollen in (d) such that the pre-swelling ratio (PSR), defined as the weight of the pre-swollen HA2 obtained in (d) to the weight of HA2 prior to pre-swelling (d) is between 20 and 200.

8. The method of claim 1, wherein the conditions of the limited crosslinking (c) satisfy one or more of the following:

$$\%m_{BDDE} = <15\% \qquad (i)$$

wherein:
% $m_{BDDE}$ is the percent weight ratio of the total weight of BDDE used in crosslinking (c) to the total weight of BDDE used in crosslinking (c) and (f), $$R = (m_{BDDE}/m_{HA1}) \times 100\% = 0.1\% \text{ to } 4.0\% \qquad (ii)$$

wherein:
R is the crosslinker ratio,
$m_{BDDE}$ is the total weight of BDDE used in crosslinking (c), and
$m_{HA1}$ is the total weight of HA1 subjected to crosslinking (c), $$X = (N_{BDDE} \times 2)/N_{DU} \times 100\% = 0.5\% \text{ to } 15\% \qquad (iii)$$

wherein:
X is the calculated theoretical maximal degree of crosslinking,
$N_{BDDE}$ is the total number of BDDE molecules used in crosslinking (c), and
$N_{DU}$ is the total number of disaccharide units (DU) of the HA1 subjected to crosslinking (c), and $$[HA1] = <100 \text{ mg/ml} \qquad (iv)$$

wherein:
[HA1] is the first hyaluronic acid (HA1) concentration prior to crosslinking, $$T = \leq 30° C., \qquad (v)$$

wherein:
T is the crosslinking temperature, $$t = 0.25 \text{ h to } 4.0 \text{ h}, \qquad (vi)$$

wherein:

t is the crosslinking time, and $$pH \leq 10. \tag{vii}$$

9. The method of claim 1, further comprising (g) subjecting the crosslinked HA1/HA2 gel composition of (f) to dialysis, and (h) sterilizing the dialyzed crosslinked HA1/HA2 gel composition of (g).

10. The method of claim 1, further comprising one or both of the following:
   adding one or more compounds, selected from the group consisting of vitamins, polyalcohols, alkali metal and alkaline earth metal salts, metals, antioxidants, local anesthetic agents, amino acids, and ceramic particles, to the crosslinked HA1/HA2 gel composition, and adjusting the pH to about 6.4 to 7.8.

11. The method of claim 1, further comprising (g) subjecting the crosslinked HA1/HA2 gel composition of (f) to dialysis, and (h) sterilizing the dialyzed crosslinked HA1/HA2 gel composition of (g), after having been filled into a syringe, by moist heat.

12. The method of claim 1, further comprising adding one or more compounds, selected from the group consisting of vitamins, alkali metal and alkaline earth metal salts, local anesthetic agents, and ceramic particles, to the crosslinked HA1/HA2 gel composition.

13. The method of claim 8, wherein the conditions of the limited crosslinking (c) satisfy two or more of (i), (ii), (iii), (iv), (v), (vi), and (vii).

14. The method of claim 8, wherein the conditions of the limited crosslinking (c) satisfy three or more of (i), (ii), (iii), (iv), (v), (vi), and (vii).

15. The method of claim 1, wherein the conditions of the crosslinking (f) satisfies one or more of the following:

$$R = (m_{BDDE}/m_{HA2}) \times 100\% = 2\% \text{ to } 12\% \tag{i'}$$

wherein:

R is the crosslinker ratio, $m_{BDDE}$ is the total weight of BDDE used in crosslinking (f), and $m_{HA2}$ is the total weight of HA2 subjected to crosslinking (f), $$X = [(N_{BDDE} \times 2)/N_{DU}] \times 100\% = 10\% \text{ to } 50\% \tag{ii'}$$

wherein:

X is the calculated maximal degree of crosslinking, $N_{BDDE}$ is the total number of BDDE molecules used in crosslinking (f), $N_{DU}$ is the total number of disaccharide units (DU) of the HA2 subjected to crosslinking (f), and $$MoD = [(N_{MONO} + N_{DOUBLE}/N_{DU}] \times 100\% = 1.0\% \text{ to } 25\%, \tag{iii'}$$

wherein:

M is the degree of modification, $N_{MONO}$ is the total number of mono-linked BBDE molecules, $N_{DOUBLE}$ is the total number of double-linked BBDE molecules, and $N_{DU}$ is the total number of disaccharide units (DU) of HA1 subjected to crosslinking (c) and HA2 subjected to crosslinking (f).

* * * * *